(12) United States Patent
Kim et al.

(10) Patent No.: US 11,851,592 B2
(45) Date of Patent: Dec. 26, 2023

(54) QUANTUM DOT-CONTAINING NANOPARTICLE AND METHOD FOR MANUFACTURING SAME

(71) Applicant: BIOSQUARE INC., Seongnam-si (KR)

(72) Inventors: Jung Won Kim, Hwaseong-si (KR); Ho Beom Song, Suwon-si (KR); Sung Wook Yoon, Anyang-si (KR)

(73) Assignee: BIOSQUARE INC., Seongnam-si (KR)

( * ) Notice: Subject to any disclaimer, the term of this patent is extended or adjusted under 35 U.S.C. 154(b) by 190 days.

(21) Appl. No.: 17/439,269

(22) PCT Filed: Mar. 19, 2020

(86) PCT No.: PCT/KR2020/095043
§ 371 (c)(1),
(2) Date: Sep. 14, 2021

(87) PCT Pub. No.: WO2020/190118
PCT Pub. Date: Sep. 24, 2020

(65) Prior Publication Data
US 2022/0195288 A1    Jun. 23, 2022

(30) Foreign Application Priority Data

Mar. 20, 2019  (KR) .................. 10-2019-0031977

(51) Int. Cl.
*C09K 11/02* (2006.01)
*C09K 11/88* (2006.01)
(Continued)

(52) U.S. Cl.
CPC .......... *C09K 11/025* (2013.01); *C09K 11/883* (2013.01); *G01N 33/54346* (2013.01);
(Continued)

(58) Field of Classification Search
CPC ..... C09K 11/025; C09K 11/883; B82Y 20/00; B82Y 40/00; G01N 33/588
See application file for complete search history.

(56) References Cited

U.S. PATENT DOCUMENTS

2021/0380876 A1*  12/2021  Jun ..................... C09K 11/02

FOREIGN PATENT DOCUMENTS

| JP | 5355456 B2 | 11/2013 |
|---|---|---|
| KR | 20090044293 A | 5/2009 |

(Continued)

OTHER PUBLICATIONS

Bong-Hyun Jun et al. Ultrasensitive, Biocompatible, Quantum-Dot-Embedded Silica Nanoparticles for Bioimaging, Advanced Functional Materials, 2012, vol. 22, pp. 1843-1849, Feb. 17, 2012.*
(Continued)

*Primary Examiner* — C Melissa Koslow
(74) *Attorney, Agent, or Firm* — STIP Law Group, LLC

(57) ABSTRACT

The present invention relates to a quantum dot-containing nanoparticle comprising: a core part; a quantum dot part bound to a surface of the core part; a shell part for protecting the core part and the quantum dot part; and a support part for supporting the binding of the core part and the shell part, wherein the nanoparticle exhibits a high occupied area and stable binding, thereby exhibiting improved luminous efficiency (QY) and brightness when detecting a biological sample (biomolecule).

13 Claims, 15 Drawing Sheets

(51) Int. Cl.
  *G01N 33/543*   (2006.01)
  *B82Y 20/00*   (2011.01)
  *B82Y 40/00*   (2011.01)
(52) U.S. Cl.
  CPC ............... *B82Y 20/00* (2013.01); *B82Y 40/00* (2013.01); *G01N 2470/04* (2021.08)

(56) References Cited

FOREIGN PATENT DOCUMENTS

| KR | 20110091740 A | | 8/2011 |
|---|---|---|---|
| KR | 20150121722 A | | 10/2015 |
| KR | 20150123189 A | | 11/2015 |
| WO | WO 2019/066567 | * | 4/2023 |

OTHER PUBLICATIONS

International Search Report of PCT/KR2020/095043, dated Jul. 1, 2020, English transltion.
San Kyeong et al, Quantum dot-assembled nanoparticles with polydiacetylene supramolecule toward label-free, multiplexed optical detection, Journal of Colloid and Interface Science, Dec. 3, 2012, vol. 394, pp. 44-48, Elsevier, Amsterdam, Netherlands.
Bong-Hyun Jun et al, Ultrasensitive, Biocompatible, Quantum-Dot-Embedded Silica Nanoparticles for Bioimaging, Advanced Functional Materials, vol. 22, pp. 1843-1849, Wiley-VCH GmbH & Co, KGaA, Weinheim, Germany.

* cited by examiner

[Fig. 1]
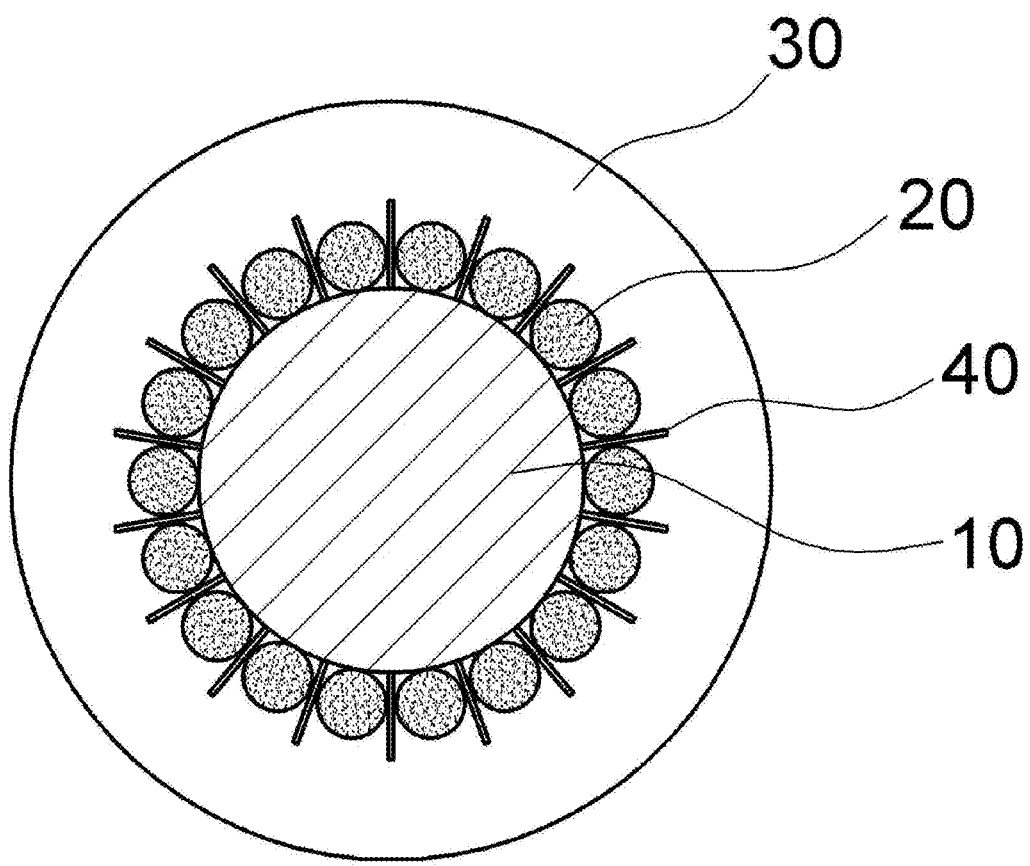

[Fig. 2]
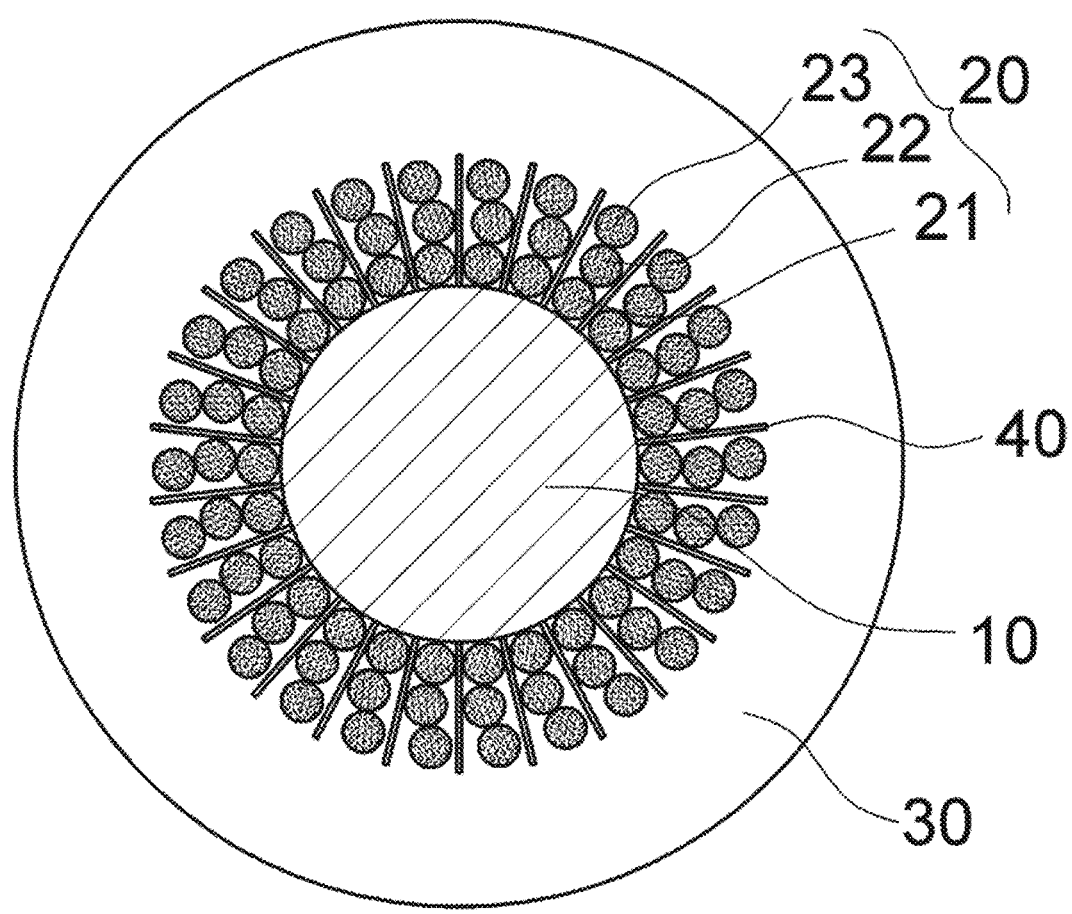

[Fig. 3]
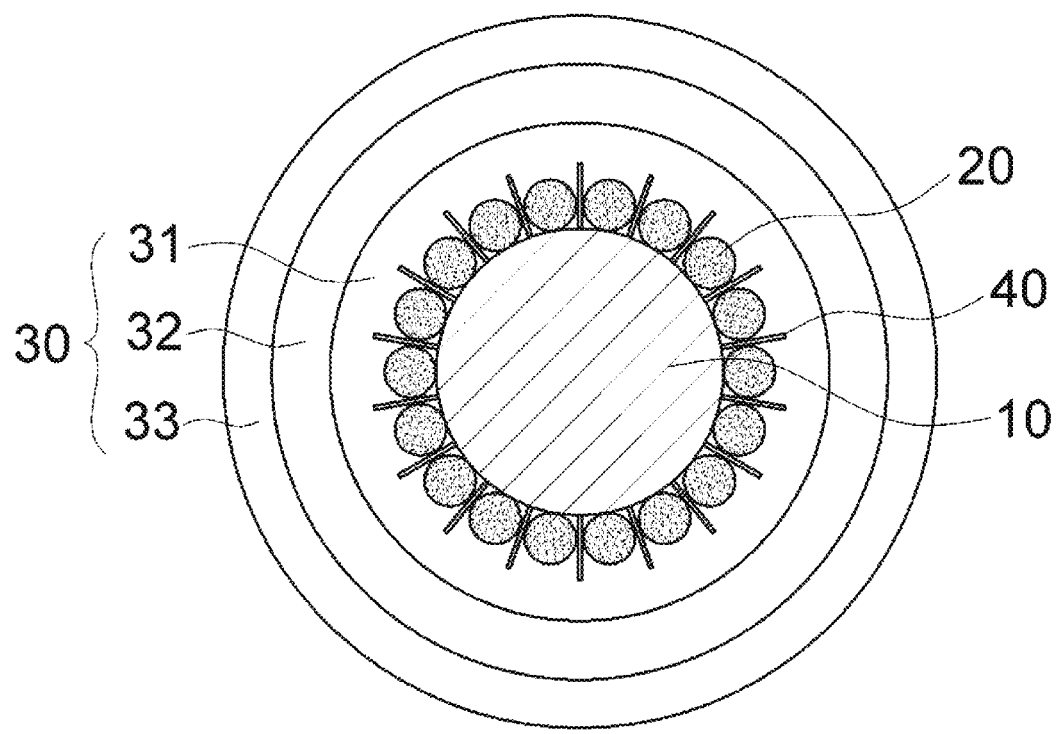

[Fig. 4]
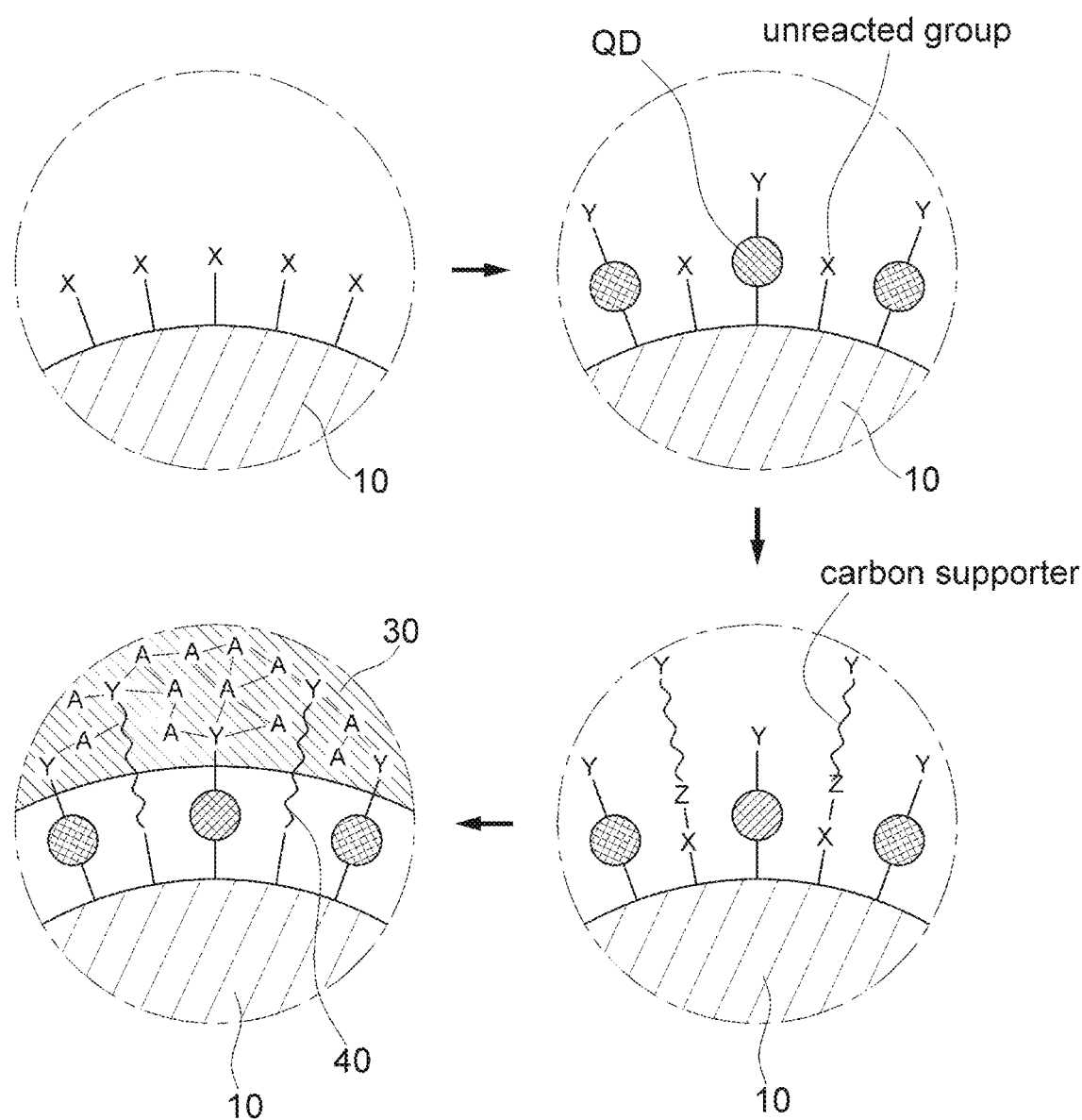

[Fig. 5]
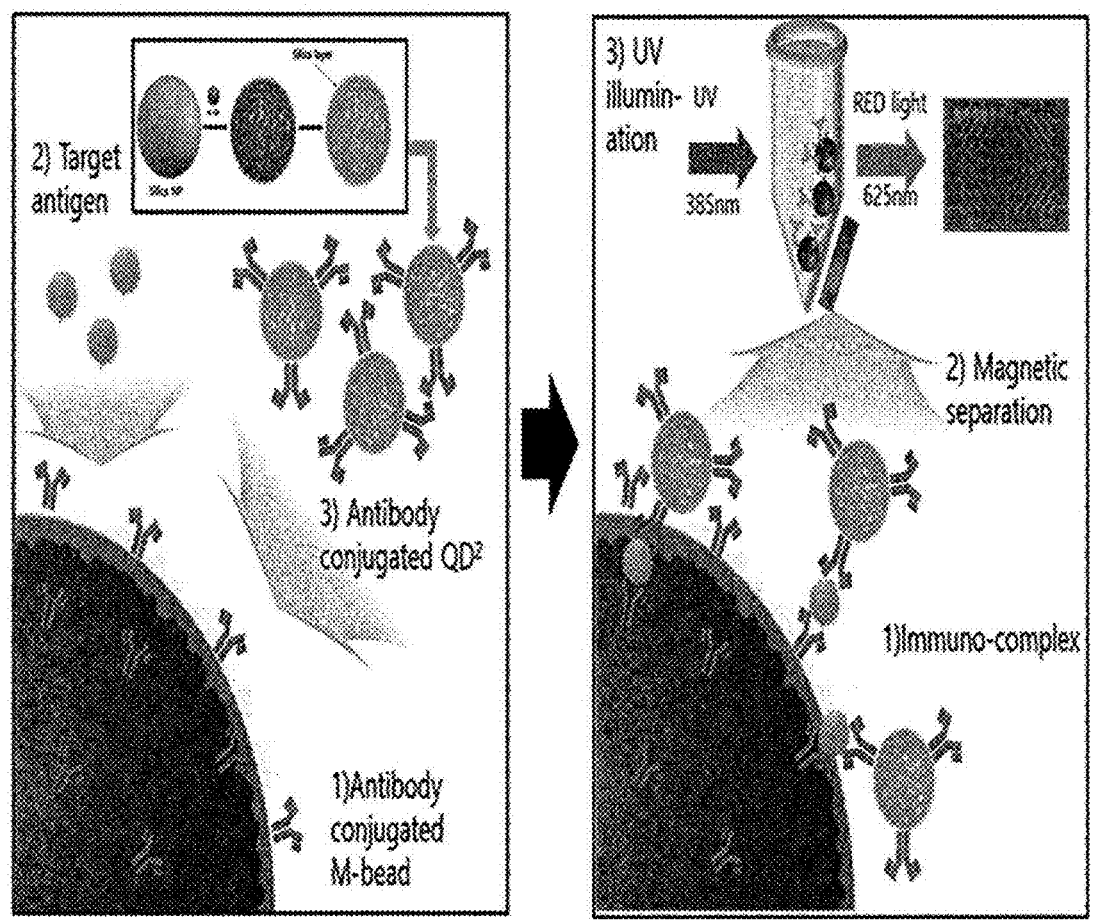

[Fig. 6]
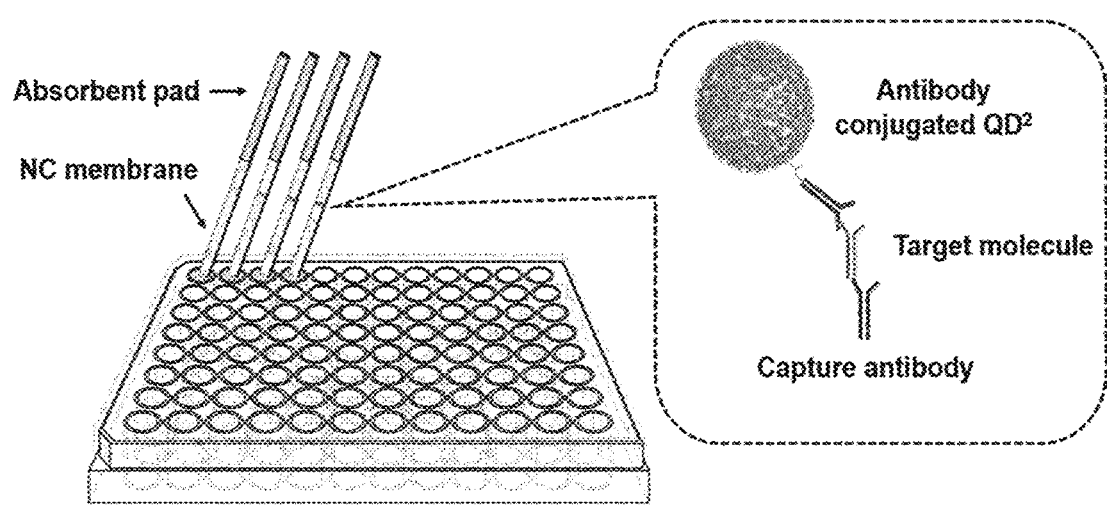

[Fig. 7A]
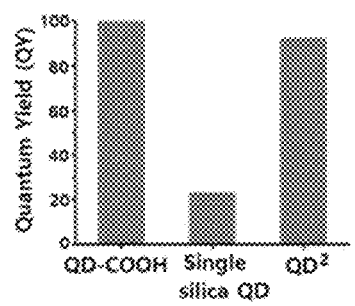
[Fig. 7B]
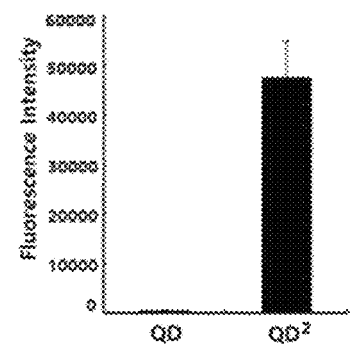
[Fig. 7C]
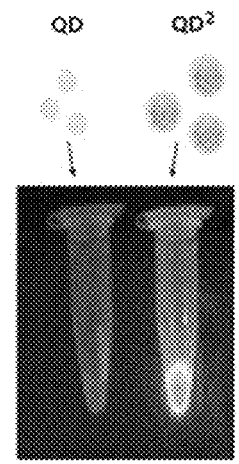

[Fig. 8]
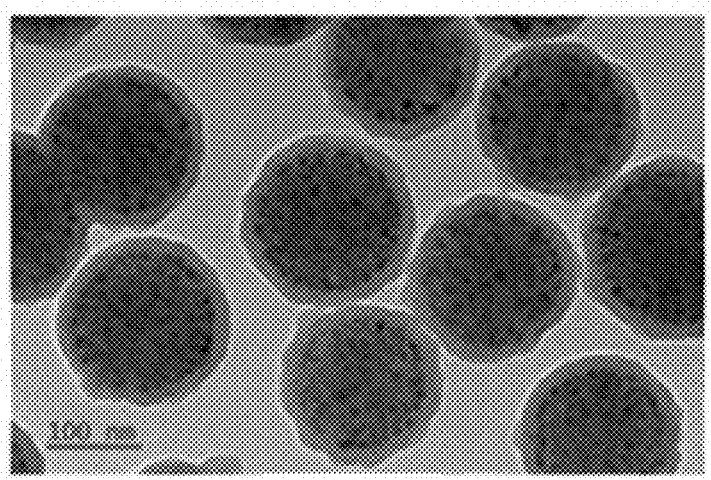
Example 3
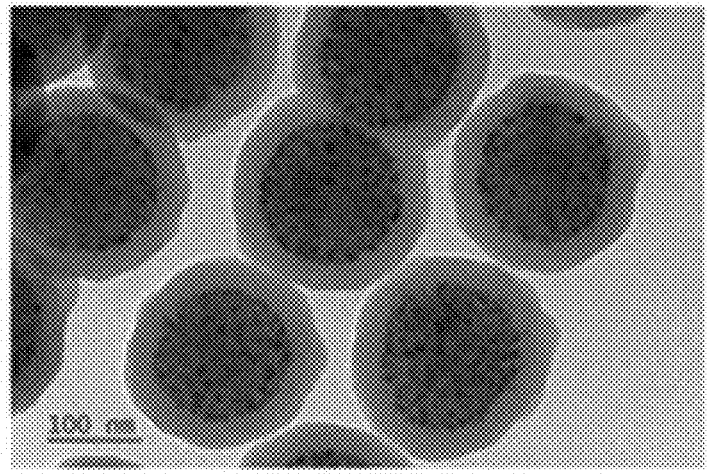
Example 4
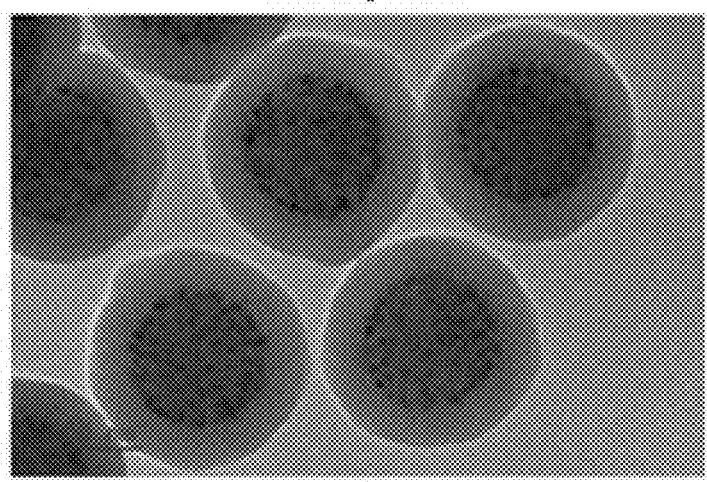
Example 5

[Fig. 9]
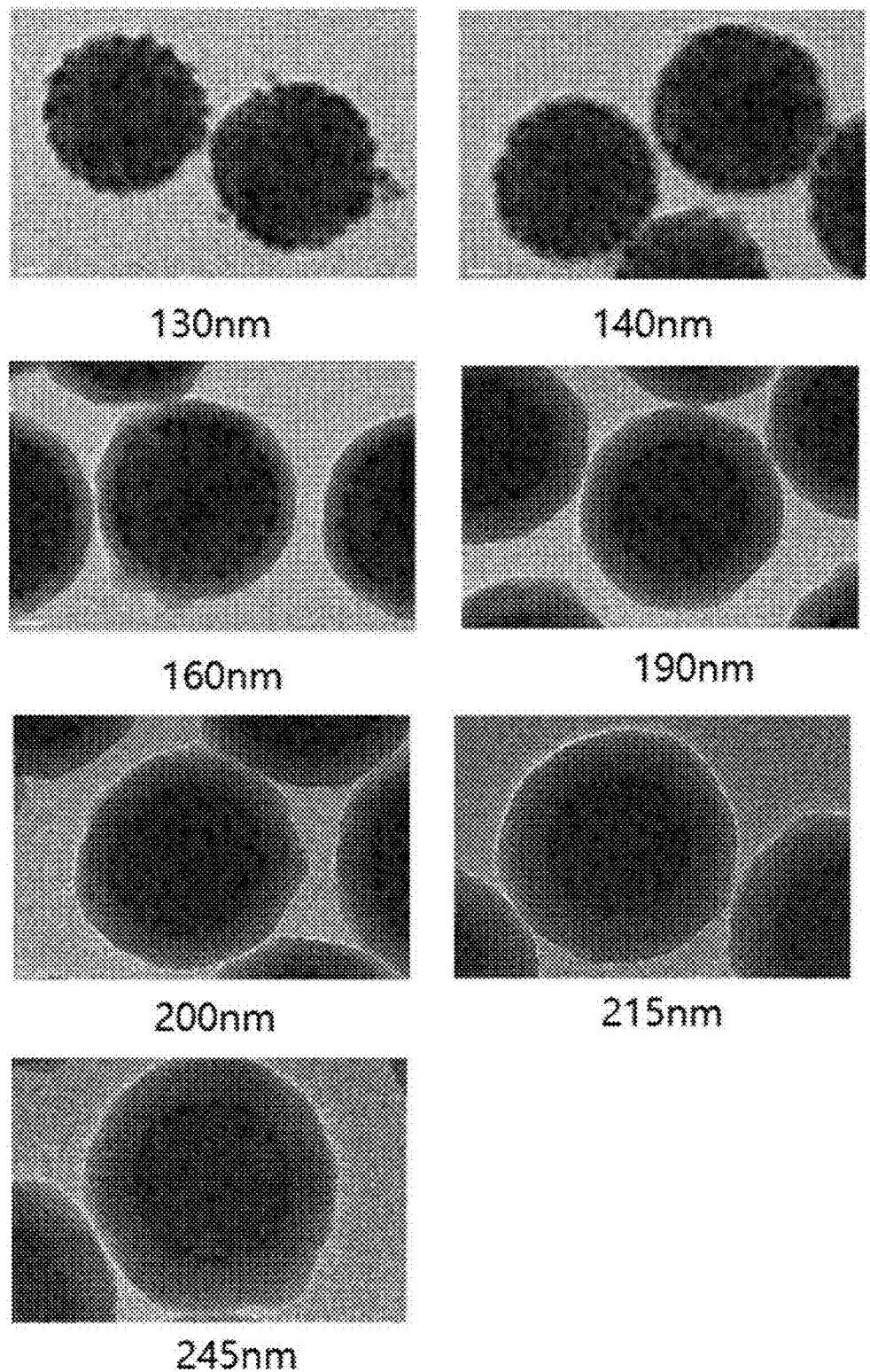

[Fig. 10]
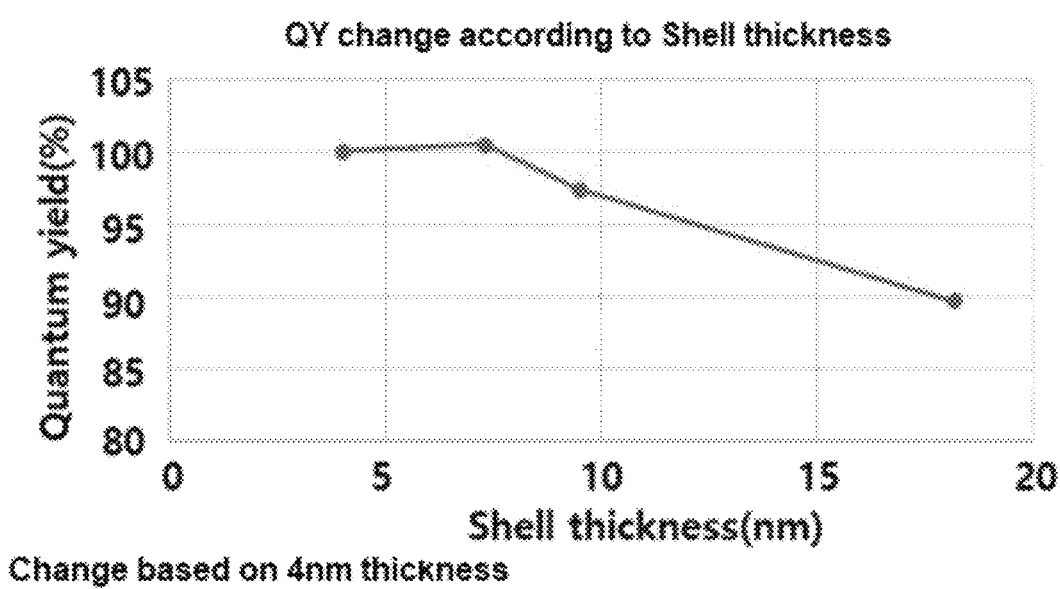

[Fig. 11]
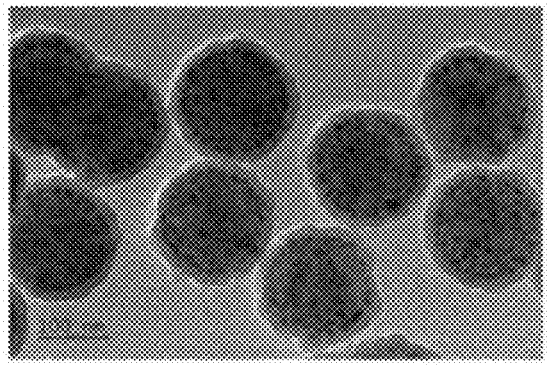
Example 10
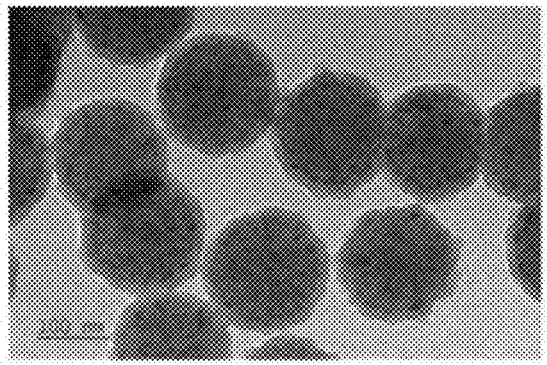
Example 11
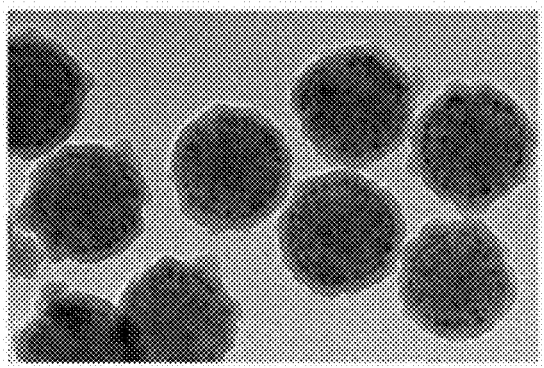
Example 12
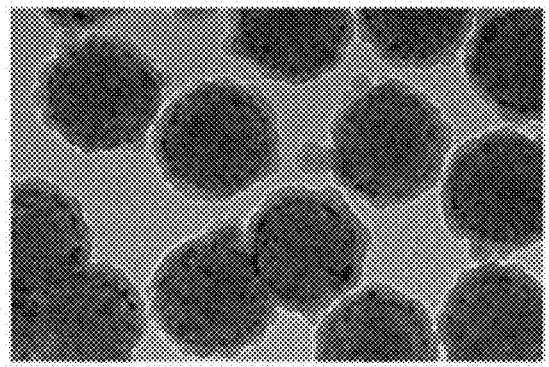
Example 13
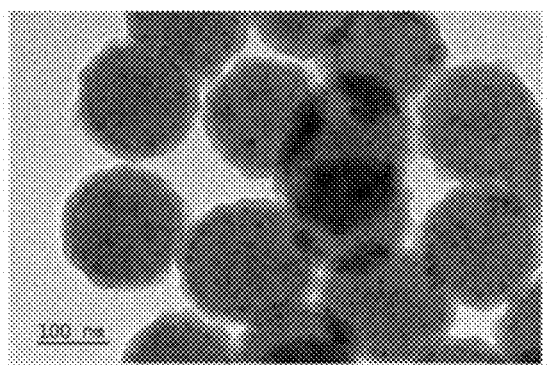
Example 14

[Fig. 12]
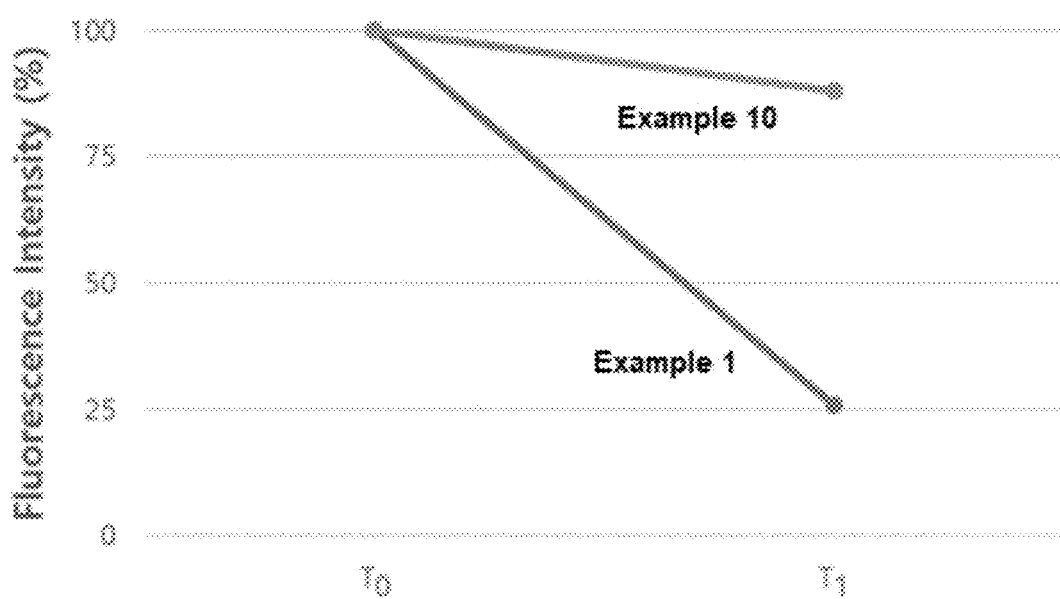

[Fig. 13A]
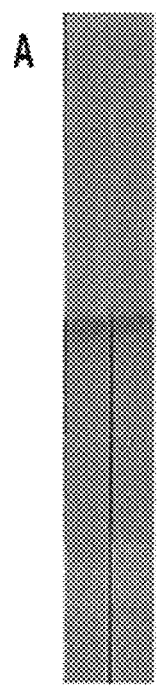
[Fig. 13B]
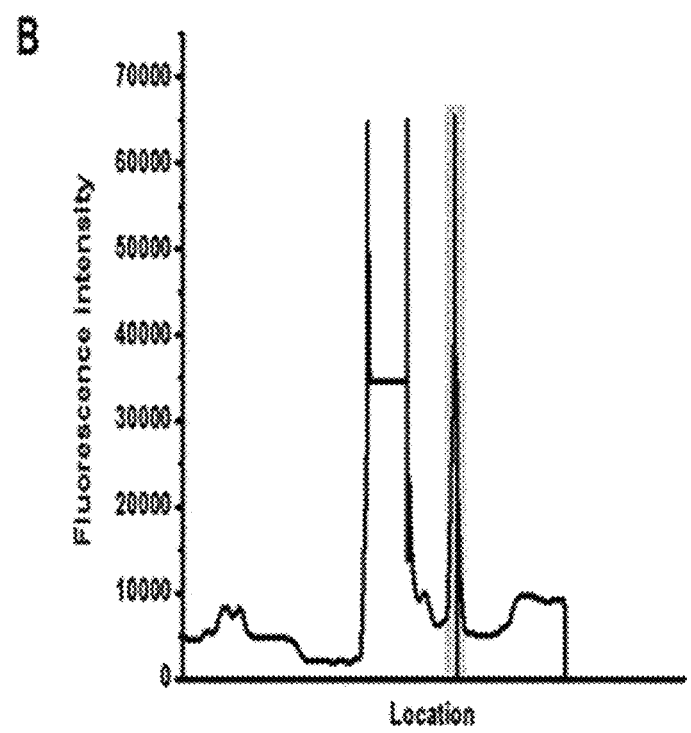

[Fig. 14A]
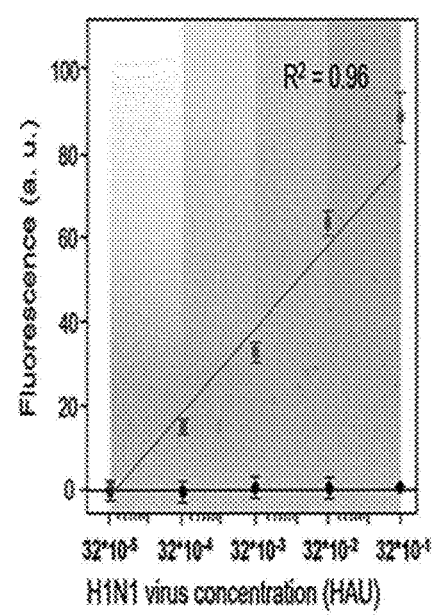
[Fig. 14B]
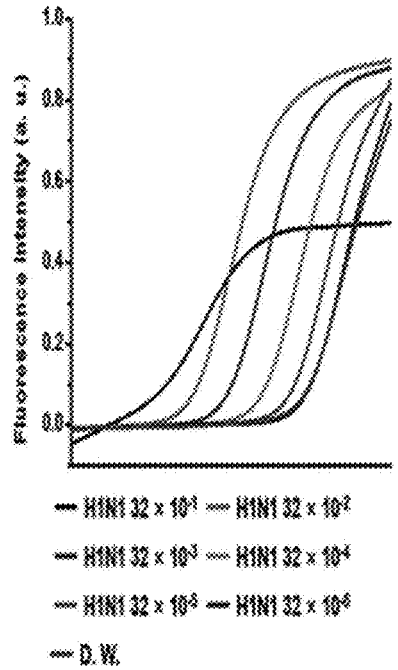

[Fig. 15A]
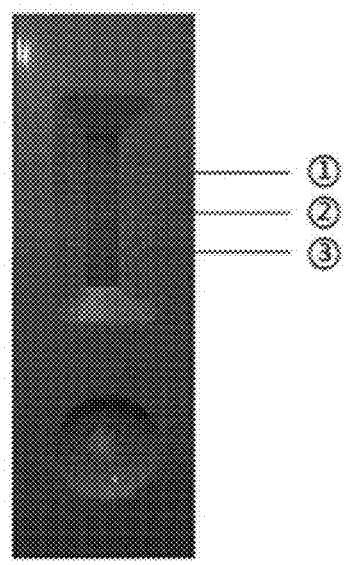
[Fig. 15B]
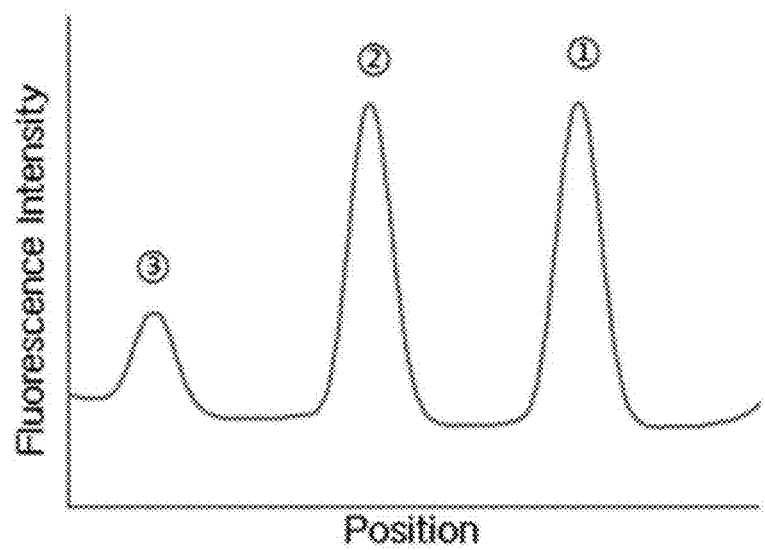

QUANTUM DOT-CONTAINING NANOPARTICLE AND METHOD FOR MANUFACTURING SAME

CROSS-REFERENCE TO RELATED APPLICATIONS

This application is the U.S. National Phase under 35 U.S.C. § 371 of International Application No. PCT/KR2020/095043 filed on Mar. 19, 2020, which in turn claims the benefit of Korean Application No. 10-2019-0031977 filed on Mar. 20, 2019, the disclosures of which are incorporated by reference into the present application.

TECHNICAL FIELD

The present invention relates to quantum dot-containing nanoparticles having various particle sizes and a method for preparing the same.

BACKGROUND ART

With the development of nanotechnology, research on biodevices fused with nanotechnology is being conducted in the bio fields related to biotechnology, new drug development, medical care, and the like. As an example, a bioplatform in which biomolecules generated by fusion of nanotechnology are immobilized in an orderly manner, preserves the activity of biomolecules compared to disordered molecular assembly and can perform a certain function for each molecule, thereby being used as a biosensor with sensitivity and excellent selectivity, which can detect fine amounts while reducing the amount of samples to be required.

A quantum dot-containing nanoparticle may be mentioned as a nanomaterial applicable to the bioplatform. The quantum dot is a semiconductor material, and is a material exhibiting a quantum confinement effect in which a luminous wavelength differs from that of a bulk state since the electron motion characteristics in the semiconductor material in the bulk state become further restricted when it becomes small to a certain size or less. If this quantum dot reaches the energy excited state by receiving light from an excitation source, it autonomously emits energy according to a corresponding energy band gap. Accordingly, since energy of various wavelength bands can be obtained by controlling the corresponding band gap of the quantum dot, the quantum dot-containing nanoparticle can exhibit optical, electrical, magnetic properties, and the like that are completely different from its original physical properties.

These quantum dot-containing nanoparticles must be protected from moisture, oxygen, light, heat, and the like, so that they can be used for a long time in bio devices while maintaining their original optical properties. Accordingly, a method of increasing the physical and chemical stability of the quantum dot-containing nanoparticles by capping the surface of the quantum dot-containing nanoparticles with a material such as silica to block the surface of the quantum dot-containing nanoparticles from contacting the outside is being applied.

However, since the quantum dots are accumulated on the capping material or the capping density is low in the process of capping the quantum dot-containing nanoparticle with a material such as silica, it is difficult to evenly distribute the quantum dots to the nanoparticle or to control the size of the nanoparticles to a required level. In addition, when the capping density is low, the stability of the quantum dot-containing nanoparticles is not secured, which leads to deterioration of the optical properties of the quantum dot-containing nanoparticles.

Accordingly, there is a need to develop quantum dot-containing nanoparticles in which the size of the particles can be freely controlled while exhibiting excellent optical properties by securing the stability of the quantum dot-containing nanoparticles.

DISCLOSURE

Technical Problem

It is an object of the present invention to provide a quantum dot-containing nanoparticle that can exhibit excellent optical properties by ensuring its stability.

It is another object of the present invention to provide a method of producing a quantum dot-containing nanoparticle in which the size of quantum dot-containing nanoparticle can be freely controlled to a required level.

It is another object of the present invention to provide a bioplatform comprising the quantum dot-containing nanoparticles.

Technical Solution

In order to solve the above problems, the present invention provides a quantum dot-containing nanoparticle comprising: a core part; a quantum dot part bound to a surface of the core part; a shell part for protecting the core part and the quantum dot part; and a support part for supporting the binding of the core part and the shell part, wherein the support part is formed of a linker having a first functional group bonded to the core part at one end and having a second functional group bonded to the shell part at the other end.

The first functional group may be one or more selected from the group consisting of a nitro group, an imide group, an ester group, a maleimide group, an iodoacetamide group, an N-hydroxysuccinimide group, and a tosyl group.

The second functional group may be one or more selected from the group consisting of an alkoxysilane group, a dialkoxysilane group, and a trialkoxysilane group.

The linker may include a linear, branched, or dendrimer-type carbon skeleton structure.

The linker may include a skeleton structure of oligoethylene glycol or polyethylene glycol.

The linker may have a molecular weight of 100 to 15,000 g/mol.

The shell part may include a plurality of silica shell layers.

The quantum dot part may include a plurality of quantum dot-embedded layers.

The ratio of (a) the diameter of the core part and (b) the thickness of the shell part may be 120 to 3:1 to 7.5.

In addition, the present invention provides a method of producing a quantum dot-containing nanoparticle, comprising the steps of: (a) modifying the surface of a core part including an organic particle or inorganic particle with a first surface modifier to form a modified core surface; (b) introducing and reacting a quantum dot to the modified core surface to form a quantum dot part; (c) introducing and reacting a linker to the quantum dot part of step (b) to form a linked quantum dot part; and (d) introducing and reacting a silica precursor to the linked quantum dot part of step (c) to form a support part and a shell part, and wherein the linker has a first functional group bonded to the core part at one end and has a second functional group bonded to the shell part at the other end.

The method of producing the quantum dot-containing nanoparticle of the present invention may further comprise the step of (c') modifying the surface of the linked quantum dot part of step (c) with a second surface modifier to form a second modified surface.

In addition, the step of (c") introducing and reacting a base to the second modified surface of step (c') to form a quantum dot part including a plurality of quantum dot-embedded layers may be further comprised.

In addition, the step of (d') performing a process of introducing and reacting a silica precursor to the support part and the shell part of step (d) one or more times to form a shell part including a plurality of silica shell layers may be further comprised.

On the one hand, the present invention provides a bioplatform comprising the quantum dot-containing nanoparticles.

Advantageous Effects

As the quantum dot-containing nanoparticle according to the present invention has a high capping density by the support part, it may secure its stability, thereby exhibiting excellent optical properties. In addition, the quantum dot-containing nanoparticle according to the present invention may exhibit various particle sizes while having excellent optical properties. Therefore, the quantum dot-containing nanoparticle according to the present invention may be usefully used in the field of biotechnology (e.g. detection of biological samples).

DESCRIPTION OF DRAWINGS

FIG. 1 is a cross-sectional view showing the quantum dot-containing nanoparticle according to an example of the present invention.

FIG. 2 is a cross-sectional view showing the quantum dot-containing nanoparticle according to another example of the present invention.

FIG. 3 is a cross-sectional view showing the quantum dot-containing nanoparticle according to another example of the present invention.

FIG. 4 is a flow chart showing a process of forming the quantum dot-containing nanoparticle according to an example of the present invention.

FIG. 5 and FIG. 6 are reference views for explaining the bioplatform according to an example of the present invention.

FIG. 7A, FIG. 7B, FIG. 7C, FIG. 8, FIG. 9, FIG. 10, FIG. 11, FIG. 12, FIG. 13A, FIG. 13B, FIG. 14A, FIG. 14B, FIG. 15A and FIG. 15B are reference views for explaining examples, experimental examples, and application examples of the present invention.

BEST MODE

The terms and words as used in the description and claims of the present invention should not be construed as limited to conventional or dictionary meanings, but should be construed as the meaning and concept consistent with the technical idea of the present invention based on the principle that the inventor can appropriately define the concept of the terms to describe its own invention in the best way.

The present invention relates to a quantum dot-containing nanoparticle that may exhibit excellent optical properties because it has excellent physical and chemical stability due to high capping density, which will be specifically described with reference to the drawings as follows.

Referring to FIG. 1, the quantum dot-containing nanoparticle (hereinafter referred to as "nanoparticle") according to the present invention may comprise a core part 10, a quantum dot part 20, a shell part 30, and a support part 40.

The core part 10 comprised in the nanoparticle of the present invention may include an organic particle or inorganic particle. The inorganic particle may be specifically one consisting of one or more components selected from the group consisting of silica, alumina, titanium dioxide, and zinc dioxide. Since these inorganic particles have high stability, when they are applied to the core part 10, the size of the nanoparticles as well as the size of the core part 10 may be easily controlled, and due to these, nanoparticles having excellent optical properties while having various particle sizes may be obtained. In addition, the inorganic particles are bound to the quantum dots by covalent bonding having a strong bonding force. In the case where they are covalently bonded, it is possible to prevent deterioration of stability due to photobleaching, and to maintain the luminous properties of quantum dots even after a long period of time.

The diameter of the core part 10 may be 10 to 100,000 nm, specifically 80 to 1,000 nm. As the diameter of the core part 10 is within the above range, handling and further post-processing of nanoparticles can be easily made.

The quantum dot part 20 comprised in the nanoparticles of the present invention is bonded to the surface of the core part 10, and may serve to enable the nanoparticles to exhibit optical properties. Specifically, the quantum dot part 20 may have a structure (a single quantum dot-embedded layer) in which a plurality of quantum dots surround the entire surface of the core part 10. In addition, the quantum dots comprised in the quantum dot part 20 may form a cross-linkage with silica, which is a component of the shell part 30, and a structure in which quantum dots are randomly bonded to the silica of the shell part 30 through the cross-linking may appear.

As an example, the quantum dots may be uniformly dispersed and bonded to the surface of the core part 10 by a material having functional groups at both ends, and due to this, the quantum dot part 20 may be formed. The material having functional groups at both ends may be specifically one to which a functional group including one or more atoms selected from the group consisting of sulfur, nitrogen, and phosphorus at one end, and one or more functional groups selected from the group consisting of a silane group, an amino group, a sulfone group, a carboxyl group, and a hydroxy group at the other end are bonded.

The quantum dots comprised in the quantum dot part 20 may have a single core structure composed of a Group II-VI series semiconductor component, a Group III-V series semiconductor component, or a Group IV-IV series semiconductor component, or may have a structure in which a coating layer is formed by coating a Group II-IV series semiconductor component on a single core.

The Group II-VI series semiconductor may be one to which at least one Group IIB element on the periodic table and at least one Group VIB element are bonded. Specifically, the Group II-VI series semiconductor may be selected from the group consisting of CdS, CdSe, CdTe, ZnSe, ZnS, PbS, PbSe, HgS, HgSe, HgTe, CdHgTe, and $CdSe_xTe_{1-x}$. The Group III-V series semiconductor may be specifically selected from the group consisting of GaAs, InAs, and InP.

Specifically, it may be more preferable in terms of luminous efficiency that the quantum dots have a structure in which a coating layer is formed on a single core rather than a single core structure. This is because the coating layer acts as a passivation layer to protect the single core, thereby increasing the stability of the quantum dots. Specifically, as the quantum dots, one in which a coating layer made of ZnS is formed on a single core made of CdSe or CdS, or one in which a coating layer made of CdSe or ZnSe is formed on a single core structure made of CdSe (Type 1 quantum dots) may be used.

In addition, as the quantum dots, one in which a hydrophobic organic compound (e.g. oleic acid) is coated on the quantum dots having a single core structure or a structure in which a coating layer is formed on a single core may be used.

The diameter of these quantum dots may be 1 to 50 nm, specifically 1 to 20 nm. In addition, when the quantum dots have a structure in which a coating layer is formed on a single core, the diameter of the single core may be 1 to 20 nm, specifically 2 to 10 nm.

The quantum dot part 20 including such quantum dots may include a plurality of quantum dot-embedded layers (quantum dot-coating layers) 21, 22, 23 as shown in FIG. 2. Specifically, the quantum dot part 20 may include a first quantum dot-embedded layer 21 surrounding the surface of the core part 10, a second quantum dot-embedded layer 22 surrounding the first quantum dot-embedded layer 21, and a third quantum dot-embedded layer 23 surrounding the second quantum dot-embedded layer 22. Wherein the number of quantum dot-embedded layers 21, 22, and 23 is not limited to that shown in FIG. 2, and may be adjusted according to the required physical properties and size of nanoparticle. In this way, when the quantum dot part 20 includes a plurality of quantum dot-embedded layers 21, 22, 23, the nanoparticle includes multi-layered multi-quantum dots, thereby exhibiting high luminous efficiency (quantum yield) and improved brightness.

The density of the layer occupied by the quantum dots in the quantum dot part 20 may be 5% or more, or 20% or more of the surface area of the core part 10 in terms of surface area occupancy. In addition, the number of quantum dots included in the quantum dot part 20 may be 10 to 400,000, 100 to 4,000, or 400 to 500.

The shell part 30 comprised in the nanoparticle of the present invention is bonded to surround the quantum dot part 20, and may serve to protect the core part 10 and the quantum dot part 20. The shell part 30 may be mainly made of silica.

The shell part 30 may include quantum dots in the process of binding to the quantum dot part 20. Specifically, as the quantum dots unbound to the quantum dot part 20 or quantum dots separated from the quantum dot part 20 are included in the shell part 30, the shell part 30 may have a quantum dot-containing composite shell structure. Wherein the number of quantum dots included in the shell part 30 may be, for example, 10 to 100,000, or 200 to 5,000. In addition, the layer density (weight/volume) occupied by the quantum dots in the shell part 30 may be 0.00001 to 99.99999%, 30 to 90%, or 7 to 80% of the virtual surface area of the quantum dot part 20.

The thickness of the shell part 30 may be 1 to 1,000 nm, specifically 1 to 300 nm. As the thickness of the shell part 30 is within the above range, it is possible to prevent the nanoparticle from becoming excessively heavy while protecting the core part 10 and the quantum dot part 20, thereby increasing the applicability of the nanoparticle.

Such a shell part 30 may include a plurality of silica shell layers 31, 32, 33 as shown in FIG. 3. Specifically, the shell part may include a first silica shell layer 31 surrounding the quantum dot part 20, a second silica shell layer 32 surrounding the first silica shell layer 31, and a third silica shell layer 33 surrounding the second silica shell layer 32. Wherein the number of silica shell layers 31, 32, and 33 is not limited to that shown in FIG. 3, and may be adjusted according to the required physical properties and size of nanoparticle. In this way, when the shell part 30 includes a plurality of silica shell layers 31, 32, 33, the capping density of the shell part 30 is increased to increase the stability of the nanoparticle. In addition, by adjusting the number of the silica shell layers 31, 32, 33, the size of the nanoparticle may be freely controlled to a required level. At this time, the size control of the nanoparticle may also be embodied by controlling the thickness by adjusting the volume of the reaction material upon the formation of the shell part 30 in addition to adjusting the number of silica shell layers 31, 32, 33 included in the shell part 30.

The support part 40 included in the nanoparticle of the present invention is bonded to the core part 10 and the shell part 30, respectively, and may serve to support the binding of the core part 10 and the shell part 30. The support part 40 may have a bridge structure connecting the core part 10 and the shell part 30. The support part 40 increases the capping density (cross-linking density) of the shell part 30 while increasing the bonding force between the core part 10 and the shell part 30, and due to these, the present invention may provide nanoparticles having high stability and excellent optical properties.

That is, referring to FIG. 4, the core part 10 has a functional group (X) to which the quantum dots (QD) may be bonded by modifying its surface for binding of the quantum dots (QD), wherein in the process of binding the quantum dots (QD), the quantum dots may not be bound to all functional groups present on the surface of the core part 10, and unreacted groups may remain. It is difficult for unreacted groups remaining on the surface of the core part 10 to bind to the shell part 30, which may lead to a decrease in the capping density of the shell part 30.

However, the present invention relates to increasing the capping density by introducing a support part 40 formed of a linker between the unreacted groups present on the core part 10 and the shell part 30, and due to this, the stability and optical properties of nanoparticle may be improved.

Specifically, the support part 40 may be formed of a linker having a first functional group (Z) bonded to the core part 10 at one end and having a second functional group (Y) bonded to the shell part 30 at the other end.

The first functional group (Z) reacts with the unreacted functional group (e.g. a thiol group) remaining on the surface of the core part 10, and specifically, may be one or more selected from the group consisting of a nitro group, an imide group, an ester group, a maleimide group, an iodoacetamide group, N-hydroxysuccinimide group, and a tosyl group.

The second functional group (Y) reacts with a silica precursor (A) for forming the shell part 30, and specifically, may be one or more selected from the group consisting of an alkoxysilane group, a dialkoxysilane group, and a trialkoxysilane group. The alkoxysilane group may be a methoxysilane group or an ethoxysilane group. The dialkoxysilane group may be a dimethoxysilane group or a diethoxysilane group. The trialkoxysilane group may be a trimethoxysilane group or a triethoxysilane group.

The linker has the first functional group and the second functional group at both ends, of which the main skeleton may have a linear, branched, or dendrimer-type carbon skeleton structure. In addition, the main skeleton of the linker may be composed of a skeleton structure of oligoethylene glycol or polyethylene glycol. When the main skeleton of the linker is composed of the skeleton structure of oligoethylene glycol or polyethylene glycol, dispersibility in a solvent (e.g. ethanol) may be improved in the process of preparing the nanoparticles.

As an example, the linker may have a structure represented by Formula 1 below:

[Formula 1]

Wherein $E_1$ is the first functional group; $E_2$ is the second functional group; $L_1$ and $L_2$ may be the same as or different from each other and may be each independently selected from the group consisting of a $C_1$-$C_{10}$ alkylene group, a $C_6$-$C_{10}$ arylene group, an ester group, an acetamide group, and a nitro group, or may be a combination thereof; and *-(PEG)$_n$-* (wherein n is an integer of 3 to 250) may be a polyethylene glycol repeating unit. Specifically, $L_1$ and $L_2$ may be each independently selected from the group consisting of a $C_1$-$C_{10}$ alkylene group,

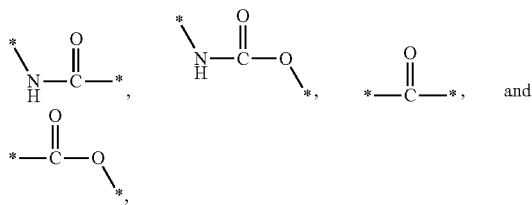

or may be a combination thereof.

On the one hand, the molecular weight of the linker may be 100 to 15,000 g/mol, and may be specifically 1000 to 10,000 g/mol.

The nanoparticle of the present invention may exhibit excellent optical properties by securing stability by the support part 40. Specifically, when the support part 40 is formed by the linker, as the linker does not simply exist in molecular units, but forms a crystal structure by the bonding between the linkers, the bonding density between the core part 10 and the shell part 30 and the cross-linking density inside the nanoparticle are improved, so that the stability of the nanoparticle may be increased.

In addition, the nanoparticles of the present invention may exhibit various sizes by controlling the thickness of the shell part 30 or the number of silica shell layers 31, 32, 33 included in the shell part 30.

Wherein considering the optical properties of the nanoparticles more, the ratio (length ratio) of (a) the diameter of the core part 10 and (b) the thickness of the shell part 30 may be 120 to 3:1 to 7.5, specifically 6 to 3:1 to 2.

In addition, the nanoparticle of the present invention may have the ratio of the diameter of the core part 10, the thickness of the quantum dot part 20, and the thickness of the shell part 30 of 1:0.1 to 9:0.1 to 10, specifically 1:0.1 to 4:0.1 to 4, more specifically 1:0.1 to 2:0.1 to 2.

On the one hand, the nanoparticle of the present invention may further comprise an outer layer part (not shown) surrounding the shell part 30. The outer layer part may be mainly made of silica, and may further include one or more components selected from the group consisting of alumina, titanium dioxide, and zinc dioxide. When the outer layer part is further included, the size of the nanoparticle may be more easily controlled due to the improvement of the template stability of nanoparticle, and centrifugation and washing may also be made possible.

The present invention provides a method of producing the above-described nanoparticle. Specifically, the method of producing the nanoparticle of the present invention may comprise the steps of: modifying the surface of a core part including an organic particle or inorganic particle with a first surface modifier to form a modified core surface (step (a)); introducing and reacting a quantum dot to the modified core surface of step (a) to form a quantum dot part (step (b)); introducing and reacting a linker to the quantum dot part of step (b) to form a linked quantum dot part (step (c)); and introducing and reacting a silica precursor to the linked quantum dot part of step (c) to form a support part and a shell part (step (d)).

Step (a) may be a process of introducing a functional group capable of binding quantum dots to the surface of a core part by reacting the core part including organic particles or inorganic particles with a first surface modifier. The first surface modifier may be a coupling agent having one or more functional groups selected from the group consisting of a silane group, a thiol group, a carbon-containing hydrophobic functional group, a carboxyl group, and an amine group at one end, and having one or more functional groups selected from the group consisting of a thiol group, an amine group, an epoxy group, halogens, and carbons at the other end. Specifically, the first surface modifier may be one or more selected from the group consisting of 3-mercaptopropyltrimethoxysilane, mercaptomethyldiethoxysilane, 3-mercaptopropylmethyldimethoxysilane, 3-mercaptopropyltriethoxysilane, 2-diphenylphosphinoethyltriethoxysilane, diphenylphosphinoethyldimethylethoxysilane, 3-aminopropylmethyldiethoxysilane, 3-aminopropyldimethylethoxysilane, 3-aminopropyltriethoxysilane, 3-aminopropyltrimethoxysilane, 4-aminobutyltrimethoxysilane, 3-(meta-aminophenoxy)propyltrimethoxysilane, and n-(2-aminoethyl)-3-aminopropylmethyldimethoxysilane.

Step (b) may be a process of forming a quantum dot part surrounding the core part by introducing and reacting quantum dots to the reactant (the core part having a modified surface) of step (a). In this case, as quantum dots, quantum dots coated with a hydrophobic organic compound may be used. In addition, a hydrophobic organic solvent is used in the process of forming the quantum dot part, so that the process of minimizing the number of unbound quantum dots and stabilizing the reaction may be performed. The hydrophobic organic solvent may be one or more selected from the group consisting of dichloromethane, dichloroethane, benzene, toluene, chlorobenzene, ethylbenzene, hexane, heptane, and cyclohexane.

The reaction ratio of the reactant (the core part having a modified surface) and the quantum dots in step (b) is not particularly limited, but considering the efficiency of the quantum dot part formation, it may be a weight ratio of 8:1 to 2:1.

Step (c) may be a process of introducing a support part-forming precursor (a state in which the first functional group of the linker is bonded to the core part) to the surface of the reactant (the surface of the core part) by reacting the quantum dot part of step (b) (the core part having the quantum dot part formed on the surface) with the linker. Since the description of the linker is the same as described above, a description thereof will be omitted.

The reaction ratio of the reactant (the core part having the quantum dot part formed on the surface) and the linker in step (c) is not particularly limited, but considering the cross-linking density of the nanoparticles, it may be a weight ratio of 10:1 to 500:1.

Step (d) may be a process of forming a support part and a shell part by reacting the linked quantum dot part of step (c) (the core part reacted with the quantum dots and the carbon support) with a silica precursor. Specifically, the silica precursor forms the support part and the shell part by reacting with the support part-forming precursor introduced in step (c). Wherein the silica precursor may be one or more selected from the group consisting of tetraethyl orthosilicate, tetramethyl orthosilicate, methyltriethoxysilane, phenyltriethoxysilane, dimethyldimethoxysilane, and ethyltriethoxysilane.

On the one hand, the method for producing the nanoparticle of the present invention may further comprise the step of modifying the linked quantum dot part of step (c) (the core part having the quantum dot part formed on the surface) with a second surface modifier (step (c')). Specifically, step (c') may be a process of introducing a functional group capable of reacting with the silica precursor, which is a shell part-forming material, on the surface of the quantum dot part (quantum dot) included in the linked quantum dot part of step (c) (the core part having the quantum dot part formed on the surface). Wherein the second surface modifier may be a coupling agent having one or more functional groups selected from the group consisting of a silane group, a thiol group, a carbon-containing hydrophobic functional group, a carboxyl group, and an amine group at one end, and having one or more functional groups selected from the group consisting of a thiol group, an amine group, an epoxy group, halogens, and carbons at the other end. Specifically, the second surface modifier may be one or more selected from the group consisting of 3-mercaptopropyltrimethoxysilane, mercaptomethyldiethoxysilane, 3-mercaptopropylmethyldimethoxysilane, 3-mercaptopropyltriethoxysilane, and 2-diphenylphosphinoethyltriethoxysilane, diphenylphosphinoethyldimethylethoxysilane, 3-aminopropylmethyldiethoxysilane, 3-aminopropyldimethylethoxysilane, 3-aminopropyltriethoxysilane, 3-aminopropyltrimethoxysilane, 4-aminobutyltrimethoxysilane, 3-(meta-aminophenoxy)propyltrimethoxysilane, and n-(2-aminoethyl)-3-aminopropylmethyldimethoxysilane. In this way, when the linked quantum dot part of step (c) is modified with the second surface modifier, the bonding density between the quantum dot part and the shell part may be increased.

Wherein the method for producing the nanoparticle of the present invention may further comprise the step of introducing and reacting a base to the second modified surface of step (c') (the core part to which the quantum dot part modified with the second surface modifier is bonded) to form a quantum dot part including a plurality of quantum dot-embedded layers (step (c")). That is, after first reacting quantum dots with the core part having the surface modified with the first surface modifier to form a first quantum dot-embedded layer, a plurality of quantum dot-embedded layers are formed by performing a process of modifying the surface with the second surface modifier, followed by performing a process of supplying a base to re-bind the quantum dots. Wherein when the binding reaction of quantum dots is carried out by supplying a base after modifying the surface with the second surface modifier, the binding between the second surface modifiers is controlled, so that a quantum dot-embedded layer having a structure in which each layer is stacked in plurality (multi-layer structure) may be easily formed. The base may be one or more selected from the group consisting of aqueous ammonia, sodium hydroxide, potassium hydroxide, calcium hydroxide, and magnesium hydroxide. In this way, when a plurality of quantum dot-embedded layers are formed, the luminous efficiency and brightness of nanoparticle may be improved.

Step (c') and/or step (c") may be performed before step (c) (i.e., reaction with the quantum dot part of step (b)), may be performed simultaneously with step (c), or may be performed after step (c).

In addition, the method of producing the nanoparticle of the present invention may further comprise the step of repeatedly performing a process of introducing and reacting a silica precursor to the support part and the shell part of step (d) one or more times (specifically, 3-4 times) to form a shell part including a plurality of silica shell layers. In this way, when a plurality of silica shell layers are formed, the size of the nanoparticle may be easily controlled to a required level.

The nanoparticles produced by the manufacturing method of the present invention may have a structure in which a large amount of quantum dots are stably bonded to the surface of the core part, may have various particle sizes, and may exhibit sufficient luminous efficiency and brightness to observe for each luminescent color. Therefore, the nanoparticles of the present invention may usefully function as a (multi) labeling site when applied to biological applications.

Specifically, the present invention may provide a bioplatform (or bioassay) comprising the above-described nanoparticles. In the present invention, the bioplatform may refer to a platform used for molecular diagnosis such as immunodiagnosis. In such a bioplatform, the nanoparticles of the present invention (specifically, the surface of the shell part of the nanoparticles) may serve as a (multi) labeling site.

As an example, the nanoparticles are conjugated to an antibody that complementarily binds to a target material (biological sample) through a ligand to provide a structure in which the nanoparticle-conjugated antibody captures the target material (biological sample). The ligand is not particularly limited, and may be a receptor-ligand pair such as streptavidin-biotin, avidin-biotin, or asialoglycoprotein-galactose.

The target material (biological sample) may be an antigen, receptor, virus, enzyme, infectious immunoglobulin, cytokine, or other infectious factor.

The bioplatform of the present invention may be embodied as a bioplatform (or bioassay) in which the above-described nanoparticles form a sandwich assay structure with a magnetic bead.

The magnetic bead may be preferably a bead-like copolymer obtained by copolymerizing a mixture of polystyrene seeds and a styrene monomer with a styrene derivative, an emulsifier, and a fat-soluble peroxide-based polymerization initiator in consideration of preventing non-specific binding.

The process of detecting the biological sample using the bioplatform of the present invention may consist of the processes of injecting a target material (biological sample) into the bioplatform in which nanoparticles and magnetic beads are arranged in a sandwich assay structure to perform a reaction (see FIG. 5), and measuring the fluorescence intensity emitted from the reaction. In this case, the fluorescence intensity may be measured through an optical method, a method of converting into an electrical signal, or the like.

On the one hand, the bioplatform of the present invention may be embodied as a biological detection kit. The biological detection kit may comprise a sensing membrane and the nanoparticles of the present invention fixed to the sensing membrane.

The sensing membrane may be one fixed by a dehydration-condensation method. In addition, the sensing membrane may be one formed on a glass plate, a polystyrene plate, or a microtiter plate.

Such a biological detection kit may be a kit capable of detecting one or more substances selected from the group consisting of monosaccharides, polysaccharides, organic acids, alcohols, cholesterol, choline, and xanthine. Specifically, FIG. 6 is a drawing showing the biological detection kit to which the nanoparticles of the present invention are applied, wherein a partial enlarged view shows the nanoparticles to which antibodies are conjugated in the red line on the nitrocellulose membrane (NC membrane) of the detection kit, and the reaction between a target material and a capture antigen.

As the biological detection kit of the present invention comprises the above-described nanoparticles (i.e., nanoparticles having various particle sizes), the sensitivity may be easily adjusted.

Hereinafter, the present invention will be described in more detail by examples. However, the following examples are only for illustrating the present invention, it will be apparent to those skilled in the art that various changes and modifications may be made within the category and the scope of the technical spirit of the present invention, and the scope of the present invention is not limited thereto.

Example 1

100 µl of 1% (v/v) 3-mercaptopropyltrimethoxysilane (MPTMS) was added to the core part made of silica particles having a diameter of 120 nm (10 mg/ml) by Stöber method, and a thiol group was introduced on the surface of the silica particles by stirring at 25° C. for 12 hours.

Next, 4 mg of solid quantum dot particles (CdSe/ZnS, 100 mg/ml) coated with oleic acid (hydrophobic) were added to the silica particles having a thiol group introduced therein, and the quantum dot particles were bounded to the thiol groups of the silica particles by vigorously stirring with a vortex. Then, 8 ml of dichloromethane, which is a hydrophobic solvent, was further added, and stirred for 10 minutes to further bind unbound quantum dot particles. Then, 100 µl of mercaptopropyltriethoxysilane (MPTES) was added thereto and stirred for 15 minutes, and then 100 µl of 25% aqueous ammonia ($NH_4OH$(aq)) as a base was added and stirred for 3 hours to form a quantum dot part having a structure in which three quantum dot-embedded layers were stacked.

Next, the nanoparticle in which the core part and the quantum dot part were formed was washed with ethanol 3 times, and then 100 µl of tetraethyl orthosilicate and 25% aqueous ammonia as a base were added thereto and stirred at 400 rpm for 20 hours to form a shell part. Thereafter, after performing a process of washing with ethanol 3 times, a quantum dot-containing nanoparticle comprising a silica core part; a quantum dot part in which three quantum dot-embedded layers were stacked; and a silica shell part (single silica shell layer) was produced.

Example 2

When forming the quantum dot part, a quantum dot-containing nanoparticle comprising a silica core part; a quantum dot part including one quantum dot-embedded layer; and a silica shell part was produced by performing the same process as in Example 1, except that 25% aqueous ammonia ($NH_4OH$(aq)) is not added after first adding and stirring mercaptopropyltriethoxysilane (MPTES), but mercaptopropyltriethoxysilane (MPTES) and 25% aqueous ammonia ($NH_4OH$(aq)) were added simultaneously and stirred.

Experimental Example 1

The luminous efficiency and brightness of the quantum dot-containing nanoparticles prepared in Examples 1 and 2 above, respectively, were measured, and the results are shown in FIG. 7. FIG. 7 is a drawing comparing luminous efficiency and brightness between the conventional quantum dot-containing nanoparticle (denoted as QD-COOH) modified with a water-soluble ligand and a COOH functional group, the multi-quantum dot-containing nanoparticle (denoted as single silica QD or QD) of Example 2, and the multi-layered multi-quantum dot-containing nanoparticle (denoted as $QD^2$) of Example 1. Referring to A in FIG. 7, the QY results of QD-COOH (Control), silica-coated QD (Example 2), and $QD^2$ (Example 1) could be confirmed; and referring to B in FIG. 7, the fluorescence intensity results of single coated QD (Example 2) and $QD^2$ (Example 1) could be confirmed. On the one hand, referring to C in FIG. 7, the results of observing single coated QD (Example 2) and $QD^2$ (Example 1) on a UV lamp (365 nm) that may be confirmed with the naked eye could be confirmed.

Example 3

A quantum dot-containing nanoparticle (average diameter of 180 nm) comprising a silica core part; a quantum dot part in which one quantum dot-embedded layer was stacked; and a silica shell part in which two silica shell layers were stacked was produced by additionally performing the process of additionally forming a shell part on the quantum dot-containing nanoparticle prepared in Example 2 one time. At this time, the process of additionally forming a shell part consisted of performing the processes of first reacting 250 µl of tetraethyl orthosilicate, 25% aqueous ammonia, ethanol, and deionized water (DW) for 25 minutes, and then adding the quantum dot-containing nanoparticle prepared in Example 2 above and stirring at 400 rpm for 20 hours, followed by washing with ethanol 3 times.

Example 4

A quantum dot-containing nanoparticle (average diameter of 210 nm) comprising a silica core part; a quantum dot part in which one quantum dot-embedded layer was stacked; and a silica shell part in which three silica shell layers were stacked was produced by additionally performing the process of forming a shell part on the quantum dot-containing nanoparticle prepared in Example 2 two times. At this time, the process of additionally forming the shell part is the process described in Example 3, and consisted of repeating this process two times.

Example 5

A quantum dot-containing nanoparticle (average diameter of 234 nm) comprising a silica core part; a quantum dot part in which one quantum dot-embedded layer was stacked; and a silica shell part in which four silica shell layers were stacked was produced by further performing the process of forming a shell part on the quantum dot-containing nanoparticle prepared in Example 2 three times. At this time, the process of additionally forming the shell part is the process described in Example 3, and consisted of repeating this process three times.

Experimental Example 2

The quantum dot-containing nanoparticles prepared in Examples 3 to 5, respectively, were analyzed by transmission electron microscopy, and the results are shown in FIG. 8. Referring to FIG. 8, it could be confirmed that the nanoparticles having an increased particle size were prepared by controlling the formation of the silica shell layer. In addition, it could be confirmed that the nanoparticles were produced in a uniform form even when the size of the nanoparticles increased.

Experimental Example 3

Quantum dot-containing nanoparticles were produced by applying any one of Examples 2 to 4, but quantum dot-containing nanoparticles having various sizes were produced by controlling the materials and reaction ratios used in each step. Thereafter, the prepared quantum dot-containing nanoparticles were analyzed by transmission electron microscopy, and the results are shown in FIG. 9. Referring to FIG. 9, it could be confirmed that quantum dot-containing nanoparticles having various sizes were prepared. This can be seen as supporting that the present invention may freely control the size of the quantum dot-containing nanoparticles.

Examples 6 to 9

Quantum dot-containing nanoparticles were produced by further performing the processes of additionally forming a shell part on the quantum dot-containing nanoparticles prepared in Example 2 once each, respectively, and the sizes of the prepared nanoparticles are shown in Table 1 below. At this time, the process of additionally forming a shell part in Example 6 consisted of performing the processes of first reacting 15 μl of tetraethyl orthosilicate, 5 μl of 25% aqueous ammonia, 5 ml of ethanol, and 0.5 ml of deionized water (DW) for 25 minutes, and then adding the quantum dot-containing nanoparticle prepared in Example 2 above and stirring at 400 rpm for 20 hours, followed by washing with ethanol 3 times. In addition, the processes of additionally forming the shell part in Examples 7, 8, and 9 consisted of performing the process of increasing and adding the amounts of the reactants (tetraethyl orthosilicate, aqueous ammonia, ethanol, and deionized water) of Example 6 by 2, 4, and 8 times, respectively, and the processes of reacting and washing, respectively.

TABLE 1

| Classification | Number of shell part formations | Nanoparticle size | Average thickness of shell part |
| --- | --- | --- | --- |
| Example 2 | 1 time | about 120 nm | about 1 nm or less |
| Example 6 | 2 times | about 128 nm | about 4 nm |
| Example 7 | 2 times | about 134 nm | about 7 nm |
| Example 8 | 2 times | about 139 nm | about 10 nm |
| Example 9 | 2 times | about 156 nm | about 18 nm |

Experimental Example 4

The stability of the quantum dot-containing nanoparticles prepared in Examples 2 and 6 to 9, respectively, was evaluated by the following method. Specifically, each of the quantum dot-containing nanoparticles of Examples 2 and 6 to 9 was put into each chamber set at 25° C., 50° C., and 70° C., and stored for 17 hours. Thereafter, the nanoparticles were taken out from the chamber to measure Quantum Yield (%) (QY), and the degree of change in QY values compared to the reference 25° C. was confirmed and shown in Table 2 below.

TABLE 2

| | QY (%) | | |
| --- | --- | --- | --- |
| Classification | 25° C. | 50° C. | 70° C. |
| Example 2 | 100 | 84.24 | 84.85 |
| Example 6 | 100 | 99.01 | 100.16 |
| Example 7 | 100 | 101.31 | 99.35 |
| Example 8 | 100 | 103.04 | 102.53 |
| Example 9 | 100 | 98.26 | 97.57 |

Referring to Table 2 above, it could be confirmed that there was no change in the QY values of the nanoparticles at 25° C., but there was a change in the QY values according to the thickness of the shell part (the number of silica shell layers) at 50° C. and 70° C., which are severe conditions. In particular, it could be confirmed that Examples 6 to 8 showed excellent stability due to small change in QY values according to the temperature.

Experimental Example 5

The change in QY values according to the increase in the average thickness of the shell part was measured using the quantum dot-containing nanoparticles prepared in Examples 6 to 9, respectively, and the results are shown in FIG. 10. Referring to FIG. 10, it could be confirmed that there was no change in the QY values until the average thickness of the shell part was about 7 nm, but the QY values decreased at a thickness of 7 nm or more.

Example 10

100 μl of 1% (v/v) 3-mercaptopropyltrimethoxysilane (MPTMS) was added to the core part made of silica particles having a diameter of 120 nm (10 mg/ml), and a thiol group was introduced on the surface of the silica particles by stirring at 25° C. for 12 hours.

Next, 4 mg of solid quantum dot particles (CdSe/ZnS, 100 mg/ml) on which the process of coating with an oleic acid (hydrophobic) was performed were added to the thiol group-introduced silica particles, and the quantum dot particles were bonded to the thiol groups of the silica particles by vigorously stirring with a vortex. Then, 8 ml of dichloromethane, which is a hydrophobic solvent, was further added, and stirred for 10 minutes to further bind unbound quantum dot particles.

Next, 150 μl of a linker (molecular weight of 1,000 g/mol) having a maleimide group and a triethoxysilane group bonded to both ends, respectively, and having a main skeleton of polyethylene glycol was added thereto and stirred for 15 minutes, followed by 100 μl of mercaptopropyltriethoxysilane (MPTES) was added thereto and stirred for 15 minutes, and then 100 μl of 25% aqueous ammonia (NH$_4$OH (aq)) as a base was added thereto and stirred for 3 hours to bind a linker to the surface of the core part while forming a quantum dot part having a structure in which three quantum dot-embedded layers were stacked.

Next, the nanoparticles to which the core part, the quantum dot part, and the linker were bonded were washed with ethanol 3 times, and then 100 µl of tetraethyl orthosilicate and 25% aqueous ammonia were added thereto and stirred at 400 rpm for 20 hours to form a support part and a shell part. Hereafter, the process of washing with ethanol 3 times was performed, and a nanoparticle comprising a silica core part; a quantum dot part in which three quantum dot-embedded layers were stacked; a linker; and a silica shell part (single silica shell layer) was produced.

Example 11

A quantum dot-containing nanoparticle was prepared by performing the same process as in Example 10 above, except that a linker having a maleimide group and a triethoxysilane group bonded to both ends, respectively, having a main skeleton of polyethylene glycol, and having a molecular weight of 2,000 g/mol was applied.

Example 12

A quantum dot-containing nanoparticle was prepared by performing the same process as in Example 10 above, except that a linker having a maleimide group and a triethoxysilane group bonded to both ends, respectively, having a main skeleton of polyethylene glycol, and having a molecular weight of 3,400 g/mol was applied.

Example 13

A quantum dot-containing nanoparticle was prepared by performing the same process as in Example 10 above, except that a linker having a maleimide group and a triethoxysilane group bonded to both ends, respectively, having a main skeleton of polyethylene glycol, and having a molecular weight of 5,000 g/mol was applied.

Example 14

A quantum dot-containing nanoparticle was prepared by performing the same process as in Example 10 above, except that a linker having a maleimide group and a triethoxysilane group bonded to both ends, respectively, having a main skeleton of polyethylene glycol, and having a molecular weight of 10,000 g/mol was applied.

Experimental Example 6

The quantum dot-containing nanoparticles prepared in Examples 10 to 14, respectively, were analyzed by transmission electron microscopy, and the results are shown in FIG. 11. Referring to FIG. 11, it could be confirmed that nanoparticles having a uniform shape and size were prepared.

Experimental Example 7

The stability of the quantum dot-containing nanoparticles prepared in Examples 1 and 10, respectively, was evaluated by the following method. Specifically, a solution containing each of the quantum dot-containing nanoparticles of Examples 1 and 10 was dropped on the pad, and then dried. Next, a chemical adhesive was dropped on the dried pad and sealed with a silver foil pouch, and then the reduction rate of the fluorescence signal (the ratio of the fluorescence signal after the lapse of storage time relative to the initial fluorescence signal) was measured while stored for 340 minutes in a chamber at 55° C., and the results are shown in FIG. 12.

Referring to FIG. 12, it could be confirmed that over time, the intensity of the fluorescence signal of Example 1 decreased by about 75%, whereas that of Example 10 decreased by about 12%. This can be seen as supporting that nanoparticles comprising a support part made of a linker have superior chemical stability compared to nanoparticles that do not comprise a support part.

[Application Example 1] Biological Detection Kit

Using the quantum dot-containing nanoparticles prepared in Example 1, a biological detection kit was prepared through the following process, and then an antigen capture experiment was performed.

1) Surface Modification of Quantum Dot-Containing Nanoparticles 1 mg of the quantum dot-containing nanoparticles of Example 1 above was added to (3-aminopropyl)triethoxysilane (APTES solution, 5% v/v, 1 mL) and stirred at room temperature for 1 hour. Thereafter, washing with ethanol was performed three times, and then 75 mg of succinic anhydride, 500 µl of 2-methyl-2-pyrrolidone (NMP) solution, and 3.50 µl of N,N-diisopropylethylamine (DIEA) were added thereto and stirred for 2 hours. Then, washing with dimethylformamide (DMF) was performed three times, and then 100 µl of dimethylpyridine (DMP) and 2.1 mg of 4-dimethylaminopyridine (DMAP) were added thereto, and 27 µl of DIC was added thereto, followed by stirring at room temperature for 1 hour. Thereafter, washing with 2-methyl-2-pyrrolidone (NMP) two times, triphosphate buffer solution (TPBS) one time, phosphate buffer solution (PBS, pH 7.2) one time was performed, respectively, and dispersed in phosphate buffer solution (PBS, pH 7.2) to perform surface modification of nanoparticles for binding the antibody.

2) Antibody Binding 20 uM antibody was added to 100 µg of surface-modified quantum dot-containing nanoparticles and stirred at room temperature for 2 hours. Then, washing with PBS (pH 7.2) was performed four times to bind the antibody to the nanoparticles.

3) Manufacture of Detection Kit

A detection kit as shown in FIG. 13-A was prepared by adding a bovine serum albumin (BSA) solution (5% w/w, 1 mL) to the quantum dot-containing nanoparticles bound to the antibody and stirring at room temperature for 1 hour.

An antigen capture experiment was performed with the prepared detection kit and the results are shown in FIG. 13. Referring to A in FIG. 13, it could be confirmed that when an antigen was captured, the capture antibody and the target material were bonded to display a mark in the line with the capture antibody on the absorbent pad side. In addition, referring to B in FIG. 13, it was possible to confirm the fluorescence intensity at the place marked with a line in the detection kit through the detection kit analysis equipment.

[Application Example 2] Bioplatform (Bioassay) Having a Sandwich Structure

Using the quantum dot-containing nanoparticles prepared in Example 1, a bioplatform was prepared through the following process, and then an experiment was performed to confirm its performance.

1) Manufacturing of Magnetic Beads

Monodisperse polystyrene seeds (4 um) were prepared using a dispersion polymerization method. As a dispersion medium, ethanol/2-methoxyethanol (volume ratio of 3:2) containing 1 g of polyvinylpyrrolidone-40 (PVP-40) was used.

Specifically, azobisisobutyronitrile (AIBN, 150 mg) was dissolved in styrene (15 mL) from which the inhibitor was removed, and then added to the dispersion medium. Thereafter, sonication was performed for 10 minutes, and then dispersion polymerization was performed in a cylindrical reaction chamber while stirring (120 cpm) at 70° C. for 20 hours. Next, polystyrene seeds (4 um, 8.3 g) were obtained by performing the processes of centrifuging the suspension and washing the precipitate with distilled water while centrifuging, and then washing with ethanol again and dried under vacuum.

Next, the obtained polystyrene seeds (4 um, 700 mg) were put in a glass reactor equipped with an overhead stirrer and a reflux condenser, and dispersed in an emulsified aqueous medium (100 mL) of dibutylphthalate (DBP, 0.7 mL) containing 0.25% (w/w) sodium dodecyl sulfate (SDS) and stirred at 400 rpm at room temperature for 20 hours to expand the polystyrene seeds with dibutylphthalate (DBP). A mixture of styrene (4.6 mL) and divinylbenzene (DVB, 2.3 mL) in which BPO (240 mg) was dissolved was placed in 100 mL of an aqueous medium containing 0.25% (w/w) sodium dodecyl sulfate (SDS), and emulsified using a homogenizer for 1 minute. Thereafter, the styrene-divinylbenzene mixture was added to a stirring polystyrene seed dispersion medium expanded with dibutylphthalate, and was reacted at room temperature at 400 rpm for 20 hours. After 20 hours, 10 ml of a 10% (w/v) aqueous polyvinyl alcohol (PVA) solution was added to the dispersion medium reacted for 20 hours, and was purged with nitrogen for 30 minutes. Thereafter, monodispersed PS-DVB beads were obtained by continuously stirring at 200 rpm at 70° C. for 20 hours for polymerization.

Next, the obtained PS-DVB beads were washed and centrifuged, and then washed with deionized water (50° C.). Then, the PS-DVB beads were washed with ethanol and tetrahydrofuran (THF), and then dibutylphthalate (DBP) and the linear polymer were removed. Thereafter, drying was performed under vacuum at 30° C. for 24 hours to obtain macroporous PS-DVB beads (7.5 μm, 2.5 g).

Next, the obtained macroporous PS-DVB beads (1 g) were put in an ice bath, and 5 ml of acetic acid was added thereto. Then, 50 mL of sulfuric acid was slowly added to the PS-DVB beads at room temperature, and was stirred for 30 minutes to 2 hours while raising the temperature to 90° C. The reaction was stopped by pouring 400 mL of ice water into the stirred dispersion, centrifuged, washed, and dried under vacuum to obtain 1.1 g of sulfonated PS-DVB beads.

Next, 500 mg of sulfonated PS-DVB beads were dispersed in 10 mL of deionized water at room temperature while purging nitrogen with mechanical stirring (200 rpm). At this time, $FeCl_3 \cdot 6H_2O$ (618 mg, 2.26 mmol) and $FeCl_2 \cdot 4H_2O$ (257 mg, 1.28 mmol) were added to the dispersion. After 2 hours, 50 mL of 28% ammonium hydroxide was added dropwise to the sulfonated PS-DVB bead dispersion for 40 minutes while continuously stirring. Thereafter, centrifugation was performed, washing with 25% trifluoroacetic acid (TFA), deionized water, and ethanol was performed, and drying was performed under vacuum to obtain 653 mg of magnetized PS-DVB beads (7.5 um).

2) Coating of Magnetized PS-DVB Beads (3-aminopropyl)triethoxysilane solution (1% (v/v), 100 mL) was added to 100 mg of magnetized PS-DVB beads and stirred at room temperature for 10 minutes. Thereafter, ammonium hydroxide (28%, 2 mL) was added thereto and stirred at room temperature for 20 minutes, and then TEOS (2 mL) was added thereto and vigorously stirred for 12 hours to coat the surface of the magnetized PS-DVB beads with silica. Next, silica-coated PS-DVB beads were collected with a magnet and washed with ethanol 5 times to obtain silica-coated PS-DVB beads.

3) Surface Modification of Silica-Coated PS-DVB Beads

The surface of the silica-coated PS-DVB beads was modified by performing the same process as in 1) surface modification of quantum dot-containing nanoparticles of Application Example 1 above.

4) Antibody Binding 10 uM antibody was added to 100 μg of the surface-modified PS-DVB beads and stirred at room temperature for 2 hours. Thereafter, washing with PBS (pH 7.2) was performed 4 times, a BSA solution (5% (w/w) 1 mL) was added thereto and stirred at room temperature for 1 hour to bind the antibody to the surface-modified PS-DVB beads.

5) Sandwich Structure Bioplatform

Antigen dispersed in PBS (pH 7.2) was added to 100 μg of antibody-bound PS-DVB beads and stirred at room temperature for 1 hour, and then washed with PBS (pH 7.2) 4 times using a magnet. Wherein 100 μg of the quantum dot-containing nanoparticles (nanoparticles of Application Example 1) bonded to the antibody were added thereto and stirred at room temperature for 1 hour, and then washed with PBS (pH 7.2) 4 times using a magnet. Next, a bioplatform was prepared by dispersing in 300 μl of PBS (pH 7.2).

An experiment was performed to confirm the performance of the prepared bioplatform, and the results are shown in FIG. 14. Referring to A in FIG. 14, the results capable of detecting the fluorescence in the range of $3.2\text{-}3.2\times10^{-4}$ HAU or more could be confirmed; and referring to B in FIG. 14, it could be confirmed that there was no significant difference when the same target material was detected in real-time PCR. This is to support that the present invention may allow accurate and rapid diagnosis at the level of real-time PCR and may provide an effect having a wide dynamic range of $\log_{10}$ or more.

[Application Example 3] Biological Detection Kit

A biological detection kit was prepared using the quantum dot-containing nanoparticles prepared in Example 10 instead of Example 1, and then an antigen capture experiment was performed. Thereafter, the detection kit was measured with a bio-only reader, and the results are shown in FIG. 15. Referring to FIG. 15, it could be confirmed that a difference in peak height appeared according to the intensity of the fluorescence signal, and it could be seen that the signal (line 3) invisible to the naked eye was confirmed as measured with a bio-only reader.

The invention claimed is:

1. A quantum dot-containing nanoparticle comprising:
   a core part;
   a quantum dot part bound to a surface of the core part;
   a shell part for protecting the core part and the quantum dot part; and
   a support part for supporting the binding of the core part and the shell part, wherein the support part is formed of a linker having a first functional group bonded to the core part at one end and a second functional group bonded to the shell part at the other end, and the first functional group is one or more selected from the group consisting of a nitro group, an imide group, an ester group, a maleimide group, an iodoacetamide group, an N-hydroxysuccinimide group, and a tosyl group.

2. The quantum dot-containing nanoparticle according to claim 1, wherein the second functional group is one or more selected from the group consisting of an alkoxysilane group, a dialkoxysilane group, and a trialkoxysilane group.

3. The quantum dot-containing nanoparticle according to claim 1, wherein the linker includes a linear, branched, or dendrimer-type carbon skeleton structure.

4. The quantum dot-containing nanoparticle according to claim 1, wherein the linker includes a skeleton structure of oligoethylene glycol or polyethylene glycol.

5. The quantum dot-containing nanoparticle according to claim 1, wherein the linker has a molecular weight of 100 to 15,000 g/mol.

6. The quantum dot-containing nanoparticle according to claim 1, wherein the shell part includes a plurality of silica shell layers, wherein the second functional group bonds to the innermost layer of the plurality of silica shell layers.

7. The quantum dot-containing nanoparticle according to claim 1, wherein the quantum dot part includes a plurality of quantum dot-embedded layers.

8. The quantum dot-containing nanoparticle according to claim 1, wherein the ratio of (a) the diameter of the core part and (b) the thickness of the shell part is 120 to 3:1 to 7.5.

9. A method of producing a quantum dot-containing nanoparticle, comprising:

(a) modifying the surface of a core part including an organic particle or inorganic particle with a first surface modifier to form a modified core surface;

(b) introducing and reacting a quantum dot to the modified core surface to form a quantum dot part;

(c) introducing and reacting a linker to the quantum dot part to form a linked quantum dot part; and (d) introducing and reacting a silica precursor to the linked quantum dot part to form a support part and a shell part, and wherein the linker has a first functional group bonded to the core part at one end and a second functional group bonded to the shell part at the other end, and the first functional group is one or more selected from the group consisting of a nitro group, an imide group, an ester group, a maleimide group, an iodoacetamide group, an N-hydroxysuccinimide group, and a tosyl group.

10. The method of producing a quantum dot-containing nanoparticle according to claim 9, further comprising the step of (c') modifying the surface of the reactant of step (c) with a second surface modifier.

11. The method of producing a quantum dot-containing nanoparticle according to claim 10, further comprising the step of (c") introducing and reacting a base to the second modified surface of step (c') to form the quantum dot part including a plurality of quantum dot-embedded layers.

12. The method of producing a quantum dot-containing nanoparticle according to claim 9, further comprising the step of (d') performing a process of introducing and reacting a silica precursor to the support part and the shell part of step (d) one or more times to form the shell part including a plurality of silica shell layers.

13. A bioplatform comprising the quantum dot-containing nanoparticles according claim 1.

\* \* \* \* \*